(12) United States Patent
Kellenberger et al.

(10) Patent No.: US 7,355,091 B2
(45) Date of Patent: Apr. 8, 2008

(54) ELASTOMERIC NONWOVEN WITH ATTACHED SUPERABSORBENT POLYMER

(75) Inventors: Stanley R. Kellenberger, Appleton, WI (US); Vincent B. Newbill, Cumming, GA (US); Daniel T. Quillin, Eden Prairie, MN (US); Wendy L. Van Dyke, Appleton, WI (US); James Hongxue Wang, Appleton, WI (US); Jennifer L. Marvin, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1120 days.

(21) Appl. No.: 10/246,800

(22) Filed: Sep. 18, 2002

(65) Prior Publication Data

US 2004/0054341 A1 Mar. 18, 2004

(51) Int. Cl.
*A61F 13/15* (2006.01)
(52) U.S. Cl. .................... 604/368; 604/367; 427/385.5
(58) Field of Classification Search ............... 604/368, 604/367; 427/385.5
See application file for complete search history.

(56) References Cited

U.S. PATENT DOCUMENTS

| 20,383 | A | 5/1858 | Whitmarsh |
|---|---|---|---|
| 1,575,003 | A | 3/1926 | Recher |
| 1,741,530 | A | 12/1929 | Mayer |
| 1,823,053 | A | 9/1931 | Lawton |
| 2,004,110 | A | 6/1935 | Head |
| 2,093,904 | A | 9/1937 | Bierer |
| 2,188,332 | A | 1/1940 | Carothers |
| 2,224,992 | A | 12/1940 | Sutherland |
| 2,353,525 | A | 7/1944 | Teague |
| 3,047,444 | A | 7/1962 | Harwood |
| 3,255,030 | A | 6/1966 | Storti |
| 3,325,338 | A | 6/1967 | Geen |
| 3,338,992 | A | 8/1967 | Kinney |
| 3,341,394 | A | 9/1967 | Kinney |
| 3,502,538 | A | 3/1970 | Petersen |
| 3,502,763 | A | 3/1970 | Hartmann |
| 3,542,615 | A | 11/1970 | Dobo et al. |
| 3,692,618 | A | 9/1972 | Dorschner et al. |
| 3,802,817 | A | 4/1974 | Matsuki et al. |
| 3,849,241 | A | 11/1974 | Butlin et al. |

(Continued)

FOREIGN PATENT DOCUMENTS

EP 0 040 087 A2 11/1981

(Continued)

OTHER PUBLICATIONS

John C. Russ: *Practical Stereology*, Plenum Press, pp. 35-39 (including contents), 1986.

*Primary Examiner*—Tatyana Zalukaeva
*Assistant Examiner*—Ginger T. Chapman
(74) *Attorney, Agent, or Firm*—Armstrong Teasdale LLP (57) ABSTRACT

Absorbent, elastomeric materials and methods of making absorbent, elastomeric materials. The absorbent, elastomeric materials include an elastomeric substrate and a superabsorbent polymer non-adhesively attached to the substrate. The elastomeric substrate includes at least one nonwoven, and may include, for example, elastic strands, elastic film, and/or elastic foam between layers of nonwoven. The superabsorbent polymer includes particles that either encase fibers of the nonwoven or bond themselves to fibers of the nonwoven.

17 Claims, 5 Drawing Sheets

U.S. PATENT DOCUMENTS

| | | |
|---|---|---|
| 3,976,075 A | 8/1976 | Chinai et al. |
| 4,318,408 A | 3/1982 | Korpman |
| 4,340,563 A | 7/1982 | Appel et al. |
| 4,381,320 A | 4/1983 | Nguyen |
| 4,443,511 A | 4/1984 | Worden et al. |
| 4,500,315 A | 2/1985 | Pieniak et al. |
| 4,525,407 A | 6/1985 | Ness |
| 4,692,368 A | 9/1987 | Taylor et al. |
| 4,721,647 A | 1/1988 | Nakanishi et al. |
| 4,778,460 A | 10/1988 | Braun et al. |
| 4,855,179 A | 8/1989 | Bourland et al. |
| 4,880,419 A | 11/1989 | Ness |
| 4,891,258 A | 1/1990 | Fahrenkrug |
| 5,021,050 A | 6/1991 | Iskra |
| 5,071,681 A | 12/1991 | Manning et al. |
| 5,098,775 A | 3/1992 | Harada et al. |
| 5,100,397 A | 3/1992 | Poccia et al. |
| 5,126,382 A | 6/1992 | Hollenberg |
| 5,139,841 A | 8/1992 | Makoui et al. |
| 5,171,237 A | 12/1992 | Poccia et al. |
| 5,226,992 A | 7/1993 | Morman |
| 5,246,429 A | 9/1993 | Poccia et al. |
| 5,422,172 A | 6/1995 | Wu |
| 5,466,731 A | 11/1995 | Akers et al. |
| 5,480,693 A | 1/1996 | Patterson et al. |
| 5,486,166 A | 1/1996 | Bishop et al. |
| 5,490,846 A | 2/1996 | Ellis et al. |
| 5,518,761 A * | 5/1996 | Hatsuda et al. ............. 427/180 |
| 5,649,916 A | 7/1997 | DiPalma et al. |
| 5,693,707 A | 12/1997 | Cheng et al. |
| 5,728,461 A * | 3/1998 | Nogata et al. ............. 428/372 |
| 5,882,769 A | 3/1999 | McCormack et al. |
| 5,962,068 A | 10/1999 | Tsuchiya et al. |
| 6,027,804 A | 2/2000 | Chou et al. |
| 6,103,358 A | 8/2000 | Brüggemann et al. ... 428/317.9 |
| 6,103,809 A | 8/2000 | Ahmed et al. |
| 6,129,801 A | 10/2000 | Benson et al. |
| 6,162,541 A | 12/2000 | Chou et al. |
| 6,203,845 B1 | 3/2001 | Qin et al. |
| 6,207,237 B1 * | 3/2001 | Haffner ...................... 427/394 |
| 6,217,692 B1 | 4/2001 | Kling |
| 6,248,851 B1 | 6/2001 | Maugans et al. |
| 6,265,045 B1 | 7/2001 | Mushaben |
| 6,362,389 B1 | 3/2002 | McDowall et al. ......... 604/367 |
| 6,369,293 B1 | 4/2002 | Reeves et al. |
| 6,417,425 B1 * | 7/2002 | Whitmore et al. .......... 604/367 |
| 6,645,407 B2 * | 11/2003 | Kellenberger et al. ...... 264/115 |
| 6,872,275 B2 * | 3/2005 | Ko et al. .................... 156/181 |
| 6,918,981 B2 * | 7/2005 | Ko et al. .................... 156/181 |
| 7,147,629 B2 * | 12/2006 | Ishikawa et al. ...... 604/385.101 |
| 2004/0051199 A1 | 3/2004 | Kellenberger et al. |
| 2004/0054342 A1 | 3/2004 | Newbill et al. |

FOREIGN PATENT DOCUMENTS

| | | |
|---|---|---|
| EP | 0 333 515 A2 | 9/1989 |
| EP | 0 188 091 B1 | 3/1991 |
| EP | 0 651 631 B1 | 2/1994 |
| EP | 0 708 119 A1 | 4/1996 |
| EP | 0 794 751 B1 | 6/1996 |
| EP | 0 947 549 A1 | 6/1998 |
| EP | 0 947 549 A1 | 10/1999 |
| EP | 1 151 735 A2 | 11/2001 |
| WO | WO 94/02094 | 2/1994 |
| WO | WO 97/15258 | 5/1997 |
| WO | WO 97/27884 | 8/1997 |
| WO | WO 97/43480 | 11/1997 |
| WO | WO 98/37846 | 9/1998 |
| WO | WO 99/10591 | 3/1999 |
| WO | WO 00/44556 | 8/2000 |
| WO | WO 00/50096 | 8/2000 |
| WO | WO 00/58546 | 10/2000 |
| WO | WO 01/56625 A2 | 8/2001 |
| WO | WO 01/87589 A2 | 11/2001 |

* cited by examiner

ELASTOMERIC NONWOVEN WITH ATTACHED SUPERABSORBENT POLYMER

BACKGROUND OF THE INVENTION

This invention is directed to absorbent, elastomeric materials and methods of making such materials.

Absorbent articles such as personal care garments, medical garments, athletic garments, workwear garments, and the like, often include both absorbent materials and elastomeric materials which, together, provide absorbency and a conforming fit. Typically, absorbent materials are not particularly elastomeric, and conversely, elastomeric materials are not particularly absorbent. The idea of a stretchable absorbent material has been around for a number of years. Examples of drawbacks encountered in attempts to combine elastomeric materials and superabsorbent materials include considerable cost in manufacturing these combinations, lack of flexibility, extensibility and elasticity in the resulting material, low levels of absorbency in terms of low intake rate as well as low fluid retention capacity, and the superabsorbent is susceptible to becoming detached from the elastomeric material.

U.S. Pat. No. 4,891,258, issued Jan. 2, 1990, teaches a stretchable absorbent garment made up of a liquid-pervious layer, a liquid-impervious layer, an absorbent layer, and a stretchable layer. The stretchable layer is stretch-bonded to the other layers and, upon relaxation, a plurality of rugosities is formed in all layers but the stretchable layer.

PCT Publication No. WO 98/37846, published Sep. 3, 1998, describes a stretchable absorbent structure having valleys. The stretch characteristics of an absorbent layer within the structure are achieved by pulling the absorbent material in a cross-machine direction or otherwise causing the material to "festoon." If the liner and outer cover are non-stretchable materials, the only stretch characteristics are provided by the unfolding of the absorbent core.

European Patent No. 0 794 751 B1, issued Jun. 2, 1999, describes a stretchable absorbent article core that is essentially a stretchable absorbent material formed by combining an elastomeric meltblown adhesive with superabsorbent materials. The adhesive is sprayed onto a forming web and the absorbent material is blown in from the side and is entangled with the adhesive fibers. This material is then integrated into an absorbent article such as a diaper.

European Patent No. 0 651 631 B1, issued Jun. 16, 1999, describes a stretchable absorbent structure including an absorbent component, such as a nonwoven, laminated to a stretchable liquid impervious component that also serves as a barrier film. The nonwoven is laminated to the film while the film is in a stretched condition. A plurality of rugosities is formed when the laminate is in a relaxed condition.

There is a need or desire for an absorbent, elastomeric material that can be used in absorbent articles such as personal care garments, medical garments, athletic garments, workwear garments, and the like, wherein the material is soft and flexible and has a high intake rate and high fluid retention capacity.

SUMMARY OF THE INVENTION

In response to the discussed difficulties and problems encountered in the prior art, a new absorbent, elastomeric material has been discovered.

The present invention is directed to absorbent, elastomeric material, and methods of making such material. This material is particularly suitable for use in personal care product applications, medical garment applications, athletic garment applications, and workwear garment applications.

The absorbent, elastomeric material of the invention is made up of an elastomeric substrate and a superabsorbent polymer non-adhesively attached to, or encasing, fibers of the substrate. As used herein, the term "non-adhesively" means that no separate adhesion material is utilized. The absorbent material has a superabsorbent retention of at least about 50% according to a stirbar retention test. Suitably, the substrate can be stretched by about 25% to about 250%. The substrate can include an elastic component bonded to one or more nonwoven facings. The nonwoven facings may be meltspun, meltblown, bonded carded web, high-loft bonded carded web, or any other suitable nonwoven. For example, the substrate may include multiple elastic strands, an elastic film, and/or an elastic foam laminated between two nonwoven facings or even an elastic foam by itself. The substrate may be either liquid-permeable or liquid-impermeable.

The invention also includes a method of making these absorbent, elastomeric materials. The superabsorbent polymer can be applied to the substrate by a number of suitable non-adhesive applications, including cross-linking after printing or spraying suitable polymer solutions, and/or polymerizing and cross-linking after applying suitable monomer solutions, thereby resulting in about 25 to 95% (based on total web weight) superabsorbent. One method, in particular, includes spraying a superabsorbent monomer particulate blend solution onto the substrate, exposing the superabsorbent solution to UV and/or other suitable radiation, and heating the irradiated solution to remove moisture, as disclosed in U.S. Pat. No. 6,417,425, issued Jul. 9, 2002, herein incorporated by reference. Another method, in particular, includes print coating a nonwoven with a superabsorbent polymer solution containing activatable cross-linkers on one or both sides of the web and activating the cross-linkers.

The superabsorbent polymer can be applied to the elastomeric substrate while the substrate is in either a stretched state or in a relaxed state. In either case, the resulting absorbent, elastomeric material is flexible, extensible, and elastic when in a relaxed state. The resulting material has a centrifuge retention capacity of between about 4 grams per gram and about 30 grams per gram.

The material of the invention is particularly suitable for use in absorbent articles, such as personal care garments, medical garments, athletic garments, and workwear garments. For example, the material can be integrated with a stretchable outer cover and liner to create a stretchable, underwear-like diaper. It can also be used in various feminine care products and adult incontinence products. It can further be used to absorb perspiration in athletic, workwear and medical garments. As yet another example, the material can be used to absorb exudates from sores and wounds and can be pretreated with a medicinal treatment, a lotion, or mixtures thereof and the like, for further advantageous use in bandages or other medical garments.

With the foregoing in mind, it is a feature and advantage of the invention to provide an absorbent, elastomeric material that can be used in absorbent articles such as personal care garments, medical garments, athletic garments, workwear garments, and the like, wherein the material is soft and flexible and has a high fluid retention capacity. The invention also includes methods of making such materials.

DEFINITIONS

Within the context of this specification, each term or phrase below will include the following meaning or meanings.

"Absorbent article" includes personal care garments, medical garments, athletic and workwear garments, and the like. The term "disposable garment" includes garments which are typically disposed of after 1-5 uses. The term "personal care garment" includes diapers, training pants, swim wear, absorbent underpants, adult incontinence products, feminine hygiene products, nursing pads, underarm pads, wipes, breathable-when-dry outer absorbent product covers, and the like. The term "medical garment" includes medical (i.e., protective and/or surgical) gowns, caps, gloves, drapes, face masks, bandages, and the like. The term "athletic garments" includes athletic socks, pants, supporters, bras, shirts, sweat bands, helmet liners, and the like. The term "workwear garments" includes laboratory coats, coveralls, hard-hat liners, and the like.

"Attached" refers to the joining, adhering, connecting, bonding, or the like, of at least two elements. Two elements will be considered to be attached together when they are attached directly to one another or indirectly to one another, such as when each is directly attached to intermediate elements.

"Bonded carded web" refers to webs made from staple length fibers that are carded into a web and then bonded by some technique such as thermal or adhesive bonding.

"Elastomeric" is the property of a material that refers to its ability to extend when under a load and recover a significant portion of the load-induced extension after the load is removed. "Elastomeric" and "elastic" are used interchangeably to refer to a material or composite that is generally capable of recovering its shape after deformation when the deforming force is removed. Specifically, as used herein, elastic or elastomeric is meant to be that property of any material which, upon application of an elongating force, permits the material to be stretchable to a stretched length which is at least about 25 percent greater than its relaxed unstretched length, and that will cause the material to recover at least 40 percent of its elongation upon release of the stretching force. A hypothetical example which would satisfy this definition of an elastomeric material would be a ten (10) centimeter sample of a material which is elongatable to at least 12.5 centimeters and which, upon being elongated to 12.5 centimeters and released, will recover to a length of less than 11.5 centimeters. Many elastic materials may be stretched by much more than 25 percent of their relaxed length, and many of these will recover to substantially their original relaxed length upon release of the stretching force.

"Elastomeric high-loft bonded carded webs" are low-density webs that contain a means of rendering them elastomeric. An example of a suitable material of this type includes two layers of through-air-bonded 17 grams per square meter (gsm) polyester with a polyethylene/polypropylene binder fiber carded web laminated to both sides of a plurality of stretched, extruded and cooled KRATON 6631 elastomeric polymer filaments, with 1.5 gsm Findley 2096 adhesive hot melt, available from Ato-Findley, Inc., Wauwatosa, Wis., sprayed on each layer of web. KRATON 6631 elastomeric polymer is available from Kraton Polymers, Belpre, Ohio.

"Encase" refers to the act of surrounding, coating, or otherwise covering an object. The term "encase" includes both total encasing and partial encasing.

"Film" refers to, for example, a thermoplastic film made using a film extrusion process, such as a cast film or blown film extrusion process. The term includes apertured films, slit films, and other porous films which constitute liquid transfer films, as well as films which do not transfer liquid.

"Foam" refers to two-phase gas-solid systems that have a supporting solid lattice of cell walls that are continuous throughout the structure. The gas, typically air, phase in a foam is usually distributed in void pockets often called cells. As used herein, "foam" is in the class of nonwovens.

"High-loft bonded carded webs" are low-density bonded carded webs often used for surge/acquisition functions in personal care garments.

"Layer" when used in the singular can have the dual meaning of a single element or a plurality of elements.

"Liquid-impermeable," when used to describe a layer or laminate means that liquid such as urine will not pass through the layer or laminate under ordinary use conditions in a direction generally perpendicular to the plane of the layer or laminate at the point of liquid contact.

"Liquid-permeable," refers to a layer or laminate that is not liquid impermeable.

"Medicinal treatment" refers to any composition that alleviates pain, discomfort, or irritation, or has any other healing or soothing properties.

"Meltblown fiber" refers to fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface.

"Meltspun fiber" refers to small diameter fibers which are formed by extruding molten thermoplastic material as filaments from a plurality of fine capillaries of a spinnerette having a circular or other configuration, with the diameter of the extruded filaments then being rapidly reduced as taught, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Meltspun fibers are quenched and generally not tacky when they are deposited onto a collecting surface. Meltspun fibers are generally continuous and often have average deniers larger than about 0.3, more particularly, between about 0.6 and 10. The term "spunbond" is often used synonymously with the term "meltspun," especially when referring to a bonded web of meltspun fibers.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, meltspinning processes, air laying processes, and bonded carded web processes. The term "nonwoven," in the most general sense, refers to any structure which is not woven and thus also includes such structures as foams.

"Open web" refers to any structure that is porous enough for fluids such as gases and liquids to pass into and/or through with relative ease.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Superabsorbent," "superabsorbent polymer," or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as polyphosphazenes, or organic compounds such as cross-linked polymers. Also included are materials which do not swell but have high enough internal capacities such as aerogels which are capable of absorbing at least about 15 times and more desirably at least about 30 times their weight in an aqueous solution containing 0.9 weight percent sodium chloride.

"Superabsorbent retention" refers to the amount of superabsorbent that remains attached to a web during or after use.

"Surge material" refers to a layer of material designed to rapidly accept fluid exudates and distribute the fluid exudates to a retention structure. Examples of suitable surge materials are described in U.S. Pat. No. 5,486,166 to Bishop et al. and U.S. Pat. No. 5,490,846 to Ellis et al., both of which are hereby incorporated by reference.

"Thermoplastic" describes a material that softens when exposed to heat and which substantially returns to a non-softened condition when cooled to room temperature.

"Thermoset" describes a material that is capable of becoming permanently cross-linked.

"Vertical filament laminate" refers to material made using a Vertical Filament Lamination (VFL) process, which is described in PCT Publication WO01/87589, published Nov. 22, 2001, and entitled ELASTIC STRANDED LAMINATE WITH ADHESIVE BONDS AND METHOD OF MANUFACTURE by H. M. Welch et al., incorporated herein by reference. This process entails vertically extruding multiple filaments onto a quench roll, elongating the filaments, laminating the filaments to a contractible (e.g. bonded carded) web and then letting the web contract thus creating, for example, an elastomeric high-loft bonded carded web.

These terms may be defined with additional language in the remaining portions of the specification.

DETAILED DESCRIPTION OF THE PRESENTLY PREFERRED EMBODIMENTS

The present invention is directed to absorbent, elastomeric material that is soft and flexible and has a high fluid retention capacity. The material can be incorporated into any suitable absorbent article, such as personal care garments, medical garments, athletic garments and workwear garments. More particularly, the material is suitable for use in diapers, training pants, swim wear, absorbent underpants, adult incontinence products, feminine hygiene products, nursing pads, underarm pads, wipes, protective medical gowns, surgical medical gowns, bandages, caps, gloves, drapes, face masks, laboratory coats, coveralls, sweatbands, athletic socks, helmet liners, hard-hat liners, and sports bras, for example. In addition, the absorbent, elastomeric material of the invention can be used in applications where an evaporative cooling effect is desired. An evaporative cooling effect can be achieved by hydrating the absorbent, elastomeric material which can be strategically located in an appropriate article such as a bandage or article of clothing.

An absorbent, elastomeric material of the invention includes an elastomeric substrate and a superabsorbent polymer attached to the substrate without the use of bonding agents such as adhesives. The method by which the superabsorbent polymer is applied to the elastomeric substrate is important because the method affects the properties of the resulting material.

The elastomeric substrate, for example, can be an elastomeric high-loft bonded carded web or can include an elastic component, such as an elastic film, an elastic foam, and/or a number of elastic strands, laminated to at least one nonwoven facing. Facing materials may be nonwovens formed using conventional processes, including bonded carded webs, or meltspun, or meltblowing processes, as described in the DEFINITIONS. For example, the facing sheets may each include a bonded carded web having a basis weight of about 3 to 150 grams per square meter (gsm), suitably 6 to 75 gsm, or about 10 to 25 gsm. The facing sheets in a single substrate may include the same or similar materials or different materials on each side of the elastomeric component. Suitably, the elastomeric substrate includes low volume fraction (VF), open web facings, having a VF of less than about 0.05, or less than about 0.04, or less than about 0.02. The VF of the open web facings is the volume of material per unit volume, and can be determined using the stereology methods taught in *Practical Stereology* by John C. Russ, published by Plenum Press, NY, N.Y. (1986). The determination of the VF of the open web facings using the stereology methods taught by Russ should be done in a manner that is representative of the VF of the facing material without the superabsorbent present. The open web facings suitably have a mean pore size greater than about 200 microns, or greater than about 400 microns, as determined using microscopic image analysis of the surface pores.

Any suitable form of bonding can be used to create the elastomeric substrate, including thermal, adhesive, or ultrasonic bonding, for example. In addition, the elastomeric substrate can consist entirely of an elastomeric foam made with suitable elasticity, cell size, and VF. The elastomeric substrate can be stretched by at least about 25%, or by at least about 50%, or by at least about 75%, and can suitably retract at least 40% of the stretched length. Ideally, the elastomeric substrate can be stretched by these amounts in more than one direction but must elastically stretch in at least one direction, suitably in the machine direction (MD). The elastomeric substrate may be either liquid-permeable or liquid-impermeable, depending on the permeability of the elastic component, regardless of whether the elastomeric substrate is in a stretched or unstretched state.

The resulting absorbent, elastomeric material of the invention can also be stretched by at least about 25%, or by at least about 50%, or by at least about 75%, and can suitably retract at least 40% of the stretched length. Ideally, the resulting absorbent, elastomeric material of the invention can be also stretched by these amounts in more than one direction but must elastically stretch in at least one direction, suitably in the machine direction (MD).

Materials suitable for use in preparing the elastic component, in the form of strands, film, and/or foam, include diblock, triblock, tetrablock, or other multi-block elastomeric copolymers such as olefinic copolymers, including styrene-isoprene-styrene, styrene-butadiene-styrene, styrene-ethylene/butylene-styrene, or styrene-ethylene/propylene-styrene, which may be obtained from Kraton Polymers, under the trade designation KRATON® elastomeric resin; polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; and single-site or metallocene-catalyzed polyolefins having density less than about 0.89 grams/cubic centimeter, available from Dow Chemical Co. under the trade name AFFINITY®.

A number of block copolymers can also be used to prepare the elastic component used in this invention. Such block copolymers generally include an elastomeric midblock portion B and a thermoplastic endblock portion A. The block copolymers may also be thermoplastic in the sense that they can be melted, formed, and resolidified several times with little or no change in physical properties (assuming a minimum of oxidative degradation). Alternatively, the elastic component can be made of a polymer that is not thermally processable, such as LYCRA® spandex, available from E. I. Du Pont de Nemours Co., or cross-linked natural rubber in film or fiber form. Thermoset polymers and polymers such as spandex, unlike the thermoplastic polymers, once cross-linked cannot be thermally processed, but can be obtained on a spool or other form and can be stretched and applied as strands in the same manner as thermoplastic polymers. As another alternative, the elastic component can be made of a thermoset polymer, such as AFFINITY®, available from Dow Chemical Co., that can be processed like a thermoplastic, i.e. stretched and applied, and then treated with radiation, such as electron beam radiation, gamma radiation, or UV radiation to cross-link the polymer, or use polymers that have functionality built into them such that they can be moisture-cured to cross-link the polymer, thus resulting in a polymer and the enhanced mechanical properties of a thermoset.

Endblock portion A may include a poly(vinylarene), such as polystyrene. Midblock portion B may include a substantially amorphous polyolefin such as polyisoprene, ethylene/propylene polymers, ethylene/butylenes polymers, polybutadiene, and the like, or mixtures thereof.

Suitable block copolymers useful in this invention include at least two substantially polystyrene endblock portions and at least one substantially ethylene/butylene mid-block portion. A commercially available example of such a linear block copolymer is available from Kraton Polymers under the trade designation KRATON® G1657 elastomeric resin. Another suitable elastomer is KRATON® G2760.

One example of making an elastomeric substrate includes the Vertical Filament Lamination of extruding one of the KRATON thermoplastic elastomeric polymers, mentioned above, from a multi-hole die onto a chilled roll. The resulting elastic strands can then be stretched by a series of rollers running at increasing speed before being laminated between lightweight high-loft bonded carded web facing materials that have been sprayed with hot melt adhesive just before entering the laminating nip. After the three parts are laminated together, the substrate can be relaxed, resulting in an elastomeric structure.

The elastic component may also contain blends of elastic and inelastic polymers, or of two or more elastic polymers, provided that the blend exhibits elastic properties.

Figure 1:
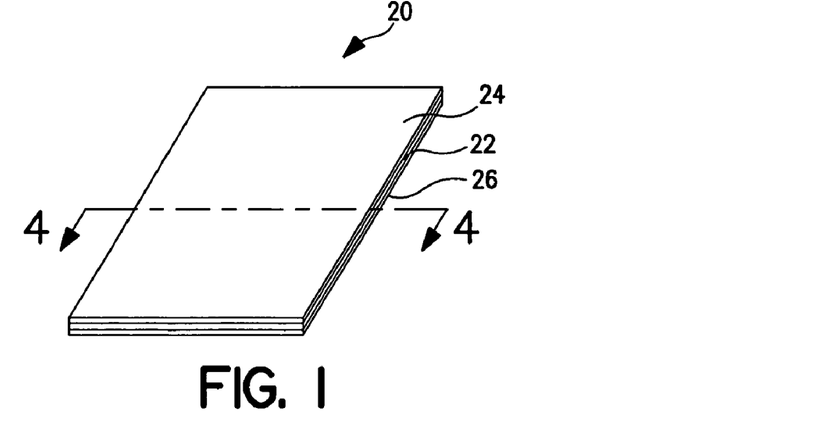
FIG. 1 is a perspective view of one embodiment of an elastomeric substrate used to make the absorbent, elastomeric material of the invention.
Figure 2:
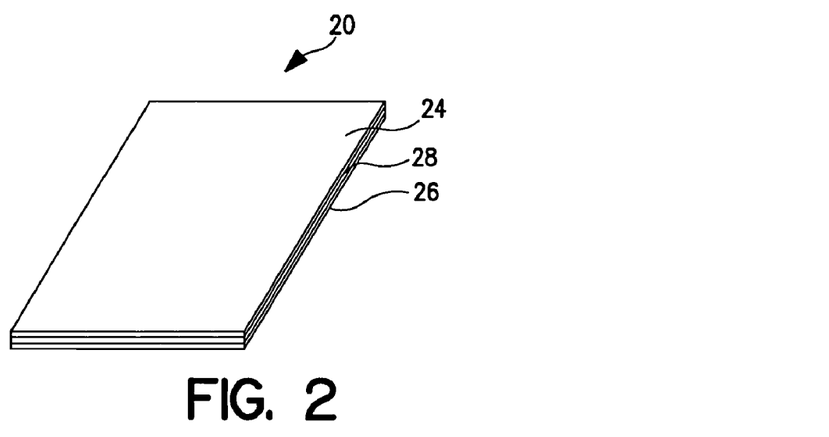
FIG. 2 is a perspective view of another embodiment of an elastomeric substrate used to make the absorbent, elastomeric material of the invention.
Figure 3:
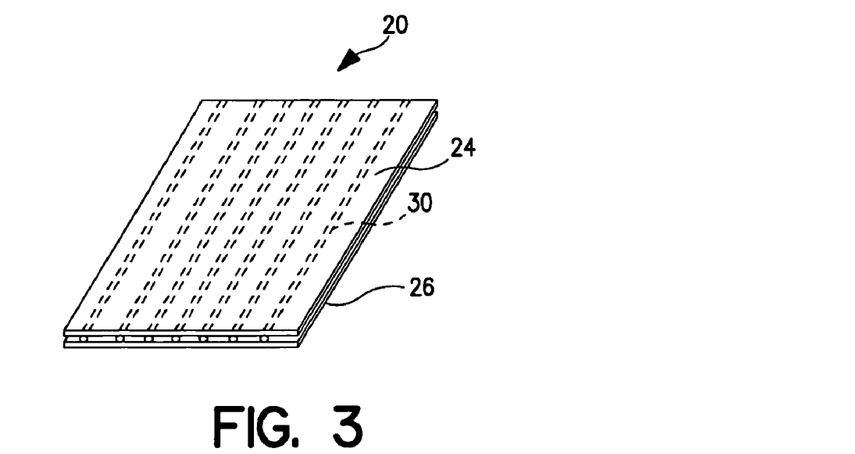
FIG. 3 is a perspective view of yet another embodiment of an elastomeric substrate used to make the absorbent, elastomeric material of the invention.
Figure 4A:
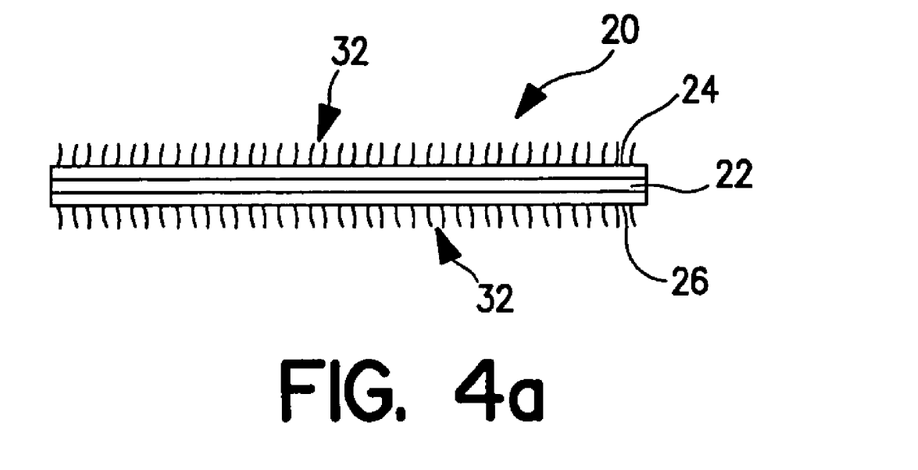
FIG. 4a is a cross-sectional view, taken along line 4-4 of FIG. 1, of one embodiment of an elastomeric substrate used to make the absorbent, elastomeric material of the invention.
Figure 4B:
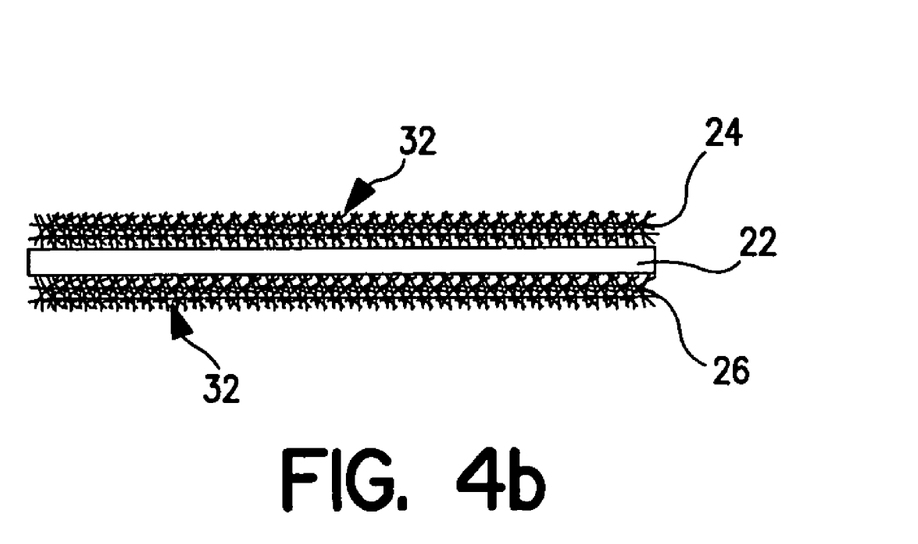
FIG. 4b is a cross-sectional view, taken along line 4-4 of FIG. 1, of another embodiment of an elastomeric substrate used to make the absorbent, elastomeric material of the invention.

FIG. 1 illustrates an elastomeric substrate 20 including an elastic film 22 laminated between two nonwoven facings 24, 26. FIG. 2 illustrates an elastomeric substrate 20 including an elastic foam 28 laminated between two nonwoven facings 24, 26. FIG. 3 illustrates an elastomeric substrate 20 including a number of elastic strands 30 laminated between two nonwoven facings 24, 26. FIG. 4a is a cross-sectional view of FIG. 1, taken along line 4-4, showing fibers 32 extending from the nonwoven facings 24, 26. FIG. 4b is a cross-sectional view of another embodiment of FIG. 1, taken along line 4-4, showing rugosities of high-loft-bonded carded web facings 24, 26, along with the fibers 32 which protrude from the irregular plane of the rugose high-loft carded web.

Figure 5A:
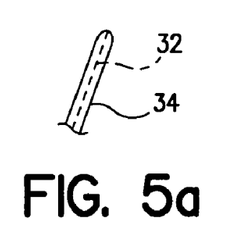
FIGS. 5a-5c illustrate fibers of the absorbent, elastomeric material of the invention with applied superabsorbent.
Figure 5B:
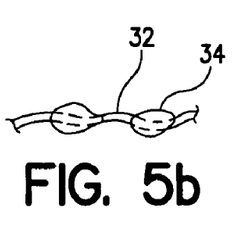
Figure 5C:
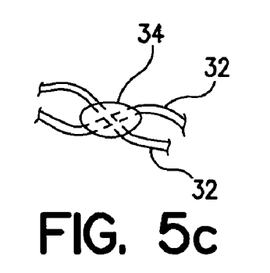

FIG. 5a illustrates a single fiber 32, representative of many fibers, of the elastomeric substrate 20 with a superabsorbent polymer 34 non-adhesively attached to, or encasing, the fiber 32. FIGS. 5b and 5c illustrate alternative types of structures. In FIG. 5b the superabsorbent polymer 34 only partially encases the fibers 32, while in FIG. 5c the superabsorbent polymer 34 encases many fibers 32.

The superabsorbent polymer 34 can include, for example, alkali metal salts of polyacrylic acids; polyacrylamides; polyvinyl alcohol; ethylene maleic anhydride copolymers; polyvinyl ethers; hydroxypropylcellulose; polyvinyl morpholinone; polymers and copolymers of vinyl sulfonic acid, polyacrylates, polyacrylamides, polyvinyl pyridine; and the like. Other suitable polymers include hydrolyzed acrylonitrile grafted starch, acrylic acid grafted starch, and isobutylene maleic anhydride copolymers and mixtures thereof. Further suitable polymers include inorganic polymers such as polyphosphazene and the like.

Typically, a superabsorbent material is capable of absorbing at least about 15 times its weight in 0.9 weight percent sodium chloride, and desirably is capable of absorbing more than about 30 times its weight in 0.9 weight percent sodium chloride. Suitable superabsorbent materials are available by, for example, following the teachings in U.S. Pat. No. 4,500,315 issued Feb. 19, 1985 to Pieniak et al., using ISOBAM 18 available from the Kuraray America, Inc. of New York, N.Y., and diethylene triamine cross-linker, or the emulsion method of PCT Publication No. WO 00/50096 published Aug. 31, 2000 by Gartner et al., or using a suitable mixture of monomer, cross-linker, and initiators per the teachings in U.S. Pat. No. 6,417,425 to Whitmore et al., or the method of U.S. Pat. No. 5,962,068 issued 05 Oct. 1999 wherein the redox initiated polymerizing superabsorbent is applied to the web early enough to surround fibers, not just to have a few particles attach to the fibers, thereby leaving the rest of the particles to attach to other particles. Each of these references relating to superabsorbent materials is hereby incorporated by reference.

The superabsorbent polymer is applied to the elastomeric substrate by surrounding fibers in the substrate or by bonding the superabsorbent to itself or to fibers in the nonwoven with, for example, crosslinkers in a superabsorbent polymer or pre-polymer solution. Crosslinking may, for example, form bonds which range from highly ionic to highly covalent types of bonds or the like. These bonds can be further augmented with hydrogen bonds and/or induced polar bonds. The superabsorbent polymer can be in a solution at a concentration of between about 5% and about 30% by weight, or between about 10% and about 25% by weight, or between about 15% and about 22% by weight, with a viscosity of between about 3,000 and about 20,000 centipoise, or between about 5,000 and about 15,000 centipoise, or between about 7,000 and about 13,000 centipoise at a shear rate of 0.1 l/s and a temperature of 22 degrees Celsius. Alternatively, the superabsorbent polymer can be formed with a suitable mixture of monomer, cross-linkers, and initiators in-situ on the web.

Figure 6:
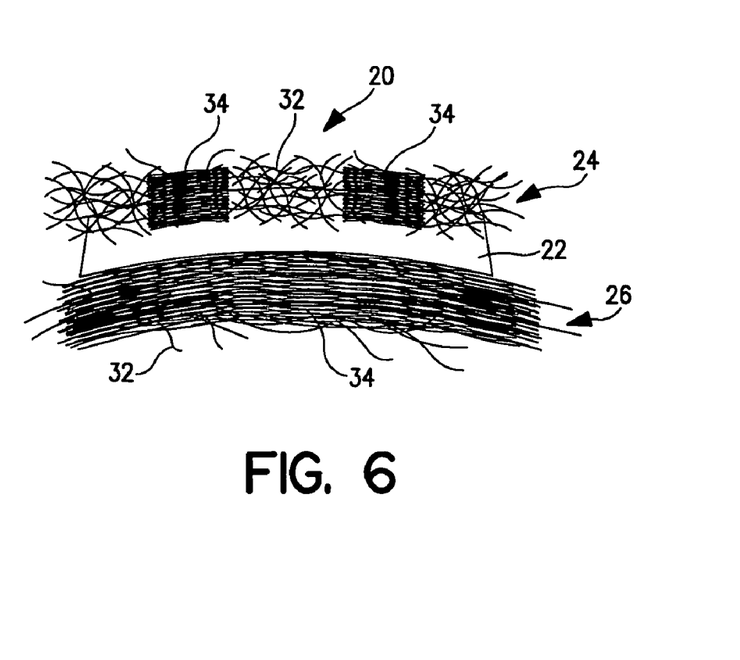
FIG. 6 illustrates the absorbent, elastomeric material of the invention with superabsorbent applied over an entire surface on one side of the material and applied in discreet areas on an opposite side of the material.

Methods of applying the superabsorbent polymer to the elastomeric substrate include saturation, printing, coating, and spraying. Examples of suitable application methods are taught in U.S. Pat. No. 4,500,315 issued Feb. 19, 1985, PCT Publication No. WO 00/50096 published Aug. 31, 2000, European Patent Application No. 0 947 549 A1 published Oct. 6, 1999, U.S. Pat. No. 6,417,425 issued Jul. 9, 2002, and in U.S. Pat. No. 5,962,068 issued Oct. 5, 1999. In one particular method, namely an in-situ polymerization superabsorbent coating process, a superabsorbent monomer solution containing monomer, crosslinkers and initiators is sprayed onto the substrate, the sprayed substrate is exposed to UV radiation and/or other radiation in order to polymerize and crosslink the monomer, and the irradiated substrate is then exposed to heat to remove any remaining moisture. In another method, the nonwoven 24, 26 is coated on one or both sides, with the superabsorbent polymer 34 either completely covering the nonwoven 26 or covering the nonwoven 24 only in discreet areas (as shown in FIG. 6), with the superabsorbent polymer containing activatable cross-linkers which are activated to cross-link the superabsorbent polymer. These methods result in about 25 to 95 percent superabsorbent polymer in the web.

The resulting superabsorbent is not in the form of particles trapped by surrounding fibers but instead is in the form of particles that encase or bond to fibers because the particles were polymerized or crosslinked while in contact with or even surrounding the fibers. Therefore, the superabsorbent material in this invention is not held onto the web by any type of adhesive, binder, or glue. Because the substrate is elastomeric both before and after the superabsorbent is applied, the superabsorbent can be applied to the substrate while the substrate is in either a relaxed or stretched state. The resulting absorbent material has enhanced superabsorbent retention because the superabsorbent is non-adhesively but firmly adhered to the nonwoven. For instance, the nonwoven retains most of the superabsorbent within the material even after reaching an equilibrium level of swelling in water, thus preventing gel escape onto skin or into the surrounding environment.

The resulting absorbent, elastomeric material is more absorbent, conformable, stretchable, softer and/or has better integrity than other absorbent structures containing superabsorbent polymer. It combines the mechanical properties of elastomeric webs with the intake and retention properties of composites containing superabsorbent. It can further provide improved intake rates due to the open structure of certain elastomeric webs with the fluid lockup capability of the superabsorbent. More particularly, the material has a centrifuge retention capacity that ranges from about 4 to about 30 grams per gram (g/g), or from about 5 g/g to about 25 g/g, or from about 6 g/g to about 20 g/g, as measured by the EDANA 441.1-99 Centrifuge Retention Capacity test wherein the complete nonwoven with superabsorbent is evaluated, and is highly dependent upon the technology used to apply the superabsorbent to the nonwoven and the properties of the superabsorbent polymer. This is a large improvement in centrifuge capacity over the original capacity of nonwoven webs which is typically less than 2.5 g/g.

A stirbar retention test, described in detail below, was used to evaluate superabsorbent retention. The test measures superabsorbent attachment to a web when the superabsorbent has been fully swollen. The test was designed to simulate the worst conditions that a superabsorbent nonwoven composite would encounter inside of a swim pant. The superabsorbent retention of the material of the invention is at least 50%, or at least 60%, or at least 70%, or at least 80%, according to the stirbar retention test.

At least some of the non-adhesively attached superabsorbent polymer is spread through at least about 50%, or at least about 75% of the thickness of the open web facing(s) of the absorbent, elastomeric material of the invention. The extent of such a spread can be determined using microscopic image analysis, as known to those skilled in the art.

Figure 7:
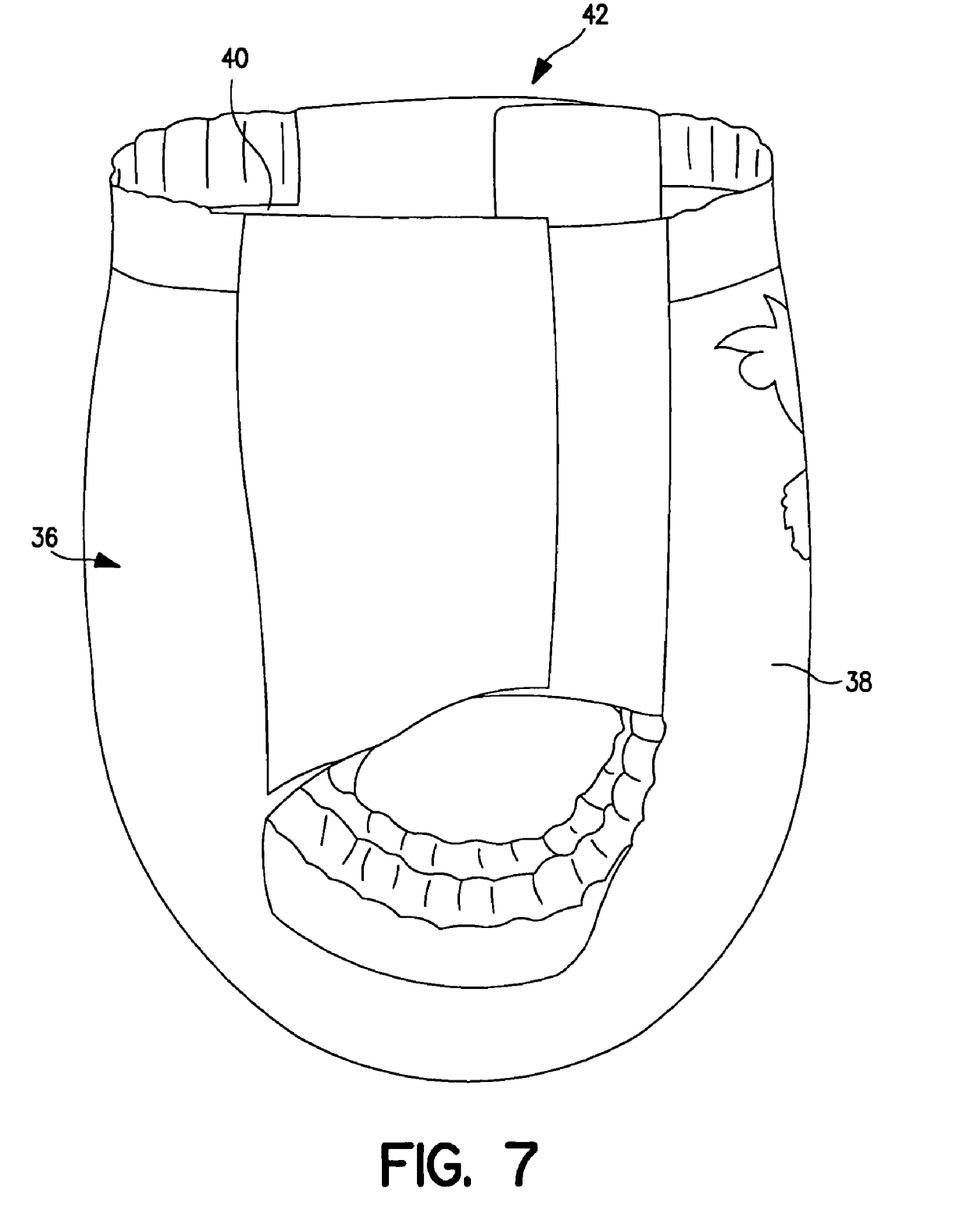
FIG. 7 is a perspective view of a garment including the absorbent, elastomeric material of the invention.
Figure 8:
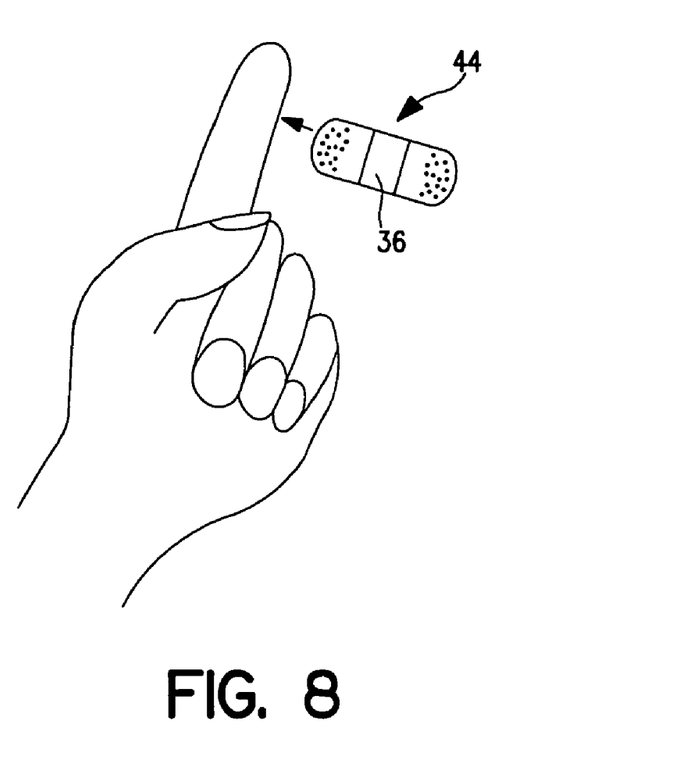
FIG. 8 is a perspective view of a bandage including the absorbent, elastomeric material of the invention.

The resulting absorbent, elastomeric material 36 is particularly suitable for use in absorbent articles. For example, the material 36 can be integrated with a stretchable outer cover 38 and liner 40 to create a stretchable, underwear-like diaper 42, as shown in FIG. 7. The material can also be used in various feminine care products and adult incontinence products. The material 36 can also be used in health care products, such as bandages. A bandage 44, shown in FIG. 8, for example, incorporating the material 36 of the invention would have elastic properties to enhance fit and absorbent properties, allowing the bandage to absorb and retain fluid released by a wound. The bandage 44 could be pretreated with a medicinal treatment that is released into the wound by the polymer. Some superabsorbent polymers, such as chitin, have been shown to have medicinal properties, thus chitin would be a particularly suitable superabsorbent polymer for use in making the absorbent, elastomeric material of the invention.

EXAMPLES

Example 1

A specific printed example was produced using an aqueous solution of ISOBAM 18 and diethylenetriamine crosslinker printed onto an elastomeric high-loft bonded carded web and then cured as taught in co-pending U.S. patent application Ser. No. 10/036,746, filed Dec. 21, 2001, by Wang et al.

The ISOBAM 18 solution used for the printing contained 20% solids and was 55% neutralized. It was generally made using the following method.
1. Mix 200 grams of ISOBAM 18 powder and 650 grams of distilled water in a laboratory reactor while heating at 80° C.
2. In a separate container, mix 56.8 grams of sodium hydroxide with 350 grams of distilled water.
3. After both solutions are well mixed, add the caustic solution dropwise to the polymer solution while continuing mixing and heating in the reactor.
4. Continue stirring and heating until the solution becomes clear.
5. Add 8 grams of diethylenetriamine to the clear solution and continue mixing and heating for 30 minutes.

Figure 9:
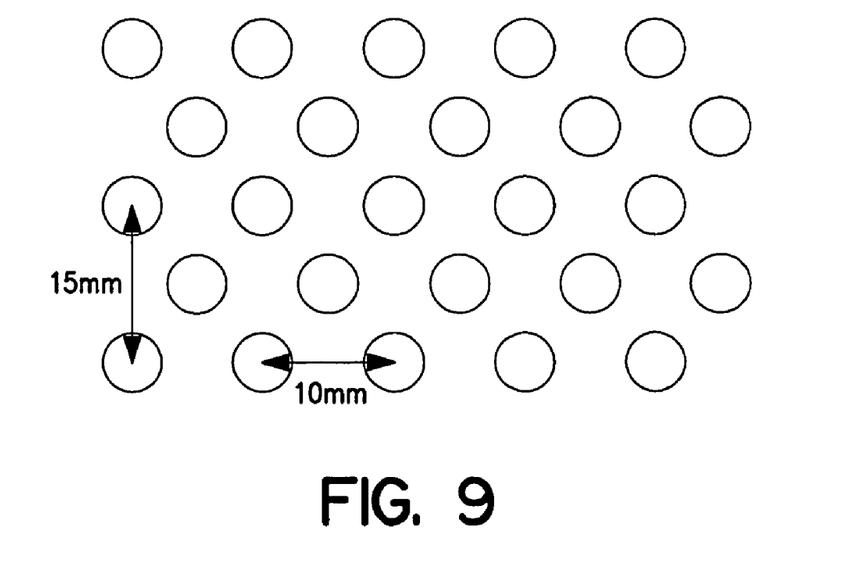
FIG. 9 illustrates one pattern for printed superabsorbent.

Once the aqueous solution was made, the solution had a viscosity, as determined by the method described in Example 2, of about 10,000 centipoise when measured at low shear rate of 0.1 l/s at 22 degrees Celsius so as to facilitate getting it into the nonwoven structure while still maintaining pattern definition. In order to control the superabsorbent location and the add-on amount, a pattern was created using an approximately 1 mm thick TEFLON sheet. Approximately 4 mm diameter holes were die cut into the sheet spaced about 15 mm apart (center to center) in the length direction and about 10 mm apart (center to center) in the width direction such that they formed an off-set staggered pattern, as shown in FIG. 9. The elastic high-loft bonded carded web example described in the Definitions section was placed under the TEFLON sheet and superabsorbent solution was forced through the holes using a 1 inch paint brush. The solution was brushed through the holes into the material until the underside of the substrate became saturated in the hole areas with superabsorbent solution. The substrate was then placed in an oven for 2 hours at a temperature of 120° C. in order to dry and crosslink the superabsorbent. Afterward the superabsorbent spots were about 5 mm in diameter. This material could be stretched over 50% and retracted almost completely. This material had a superabsorbent retention of greater than 70% when tested by the Stirbar Retention Test.

Example 2

ISOBAM-18 is poly(isobutylene-co-maleic anhydride) having a molecular weight of about 300,000 to 350,000 g/mole. The more detailed procedure for making the printable superabsorbent polymer solution in Example 1 (Sample 1) is provided as follows: In a 2-liter PYREX glass resin kettle reactor (5.25 inches diameter and 7 inches in height), 200 grams of ISOBAM-18 powder and 650 grams of de-ionized water were added. The reactor was equipped with an overhead motor driven blade stirrer, a thermocouple for measuring temperatures, and a liquid addition funnel. The mixture was heated by a heating mantle which was controlled by a DYNA SENSE controller, Model 2157, supplied by Cole-Parmer Instrument Company, Chicago, Ill. The resulting mixture was stirred by a heavy-duty laboratory motor Type 6T-10, 115 volts DC, 0.6 amp, ¹/₂₀ HP, manufactured by G. K. Heller Corp., Floral Park, N.Y. The motor was controlled by a Series S motor controller manufactured by G. K. Heller Corp. at a setting of 7 or higher. The temperature was set to 80 degrees Celsius. A white slurry resulted from the mixture.

For Sample 1, a solution of sodium hydroxide was obtained by adding 54.2 grams of reagent grade sodium hydroxide, from Aldrich, and 350 grams of de-ionized water into a 500 ml beaker. The mixture was stirred by a magnetic stirring bar on a stirring plate.

When the temperature of mixture in the resin kettle reached the set temperature (80 degrees Celsius), the sodium hydroxide solution was added to the mixture dropwise through the liquid addition funnel. The mixture was again stirred at the set temperature for 4 hours. A translucent solution resulted. 8 grams of diethylenetriamine (Aldrich) was then added to the solution. The resulting solution was a solution of the liquid superabsorbent precursor.

In Sample 2, the sodium hydroxide was increased to 56.8 g, while all the other conditions were kept the same as Sample 1. In Sample 3, the sodium hydroxide was increased to 59.4 g, while all the other conditions were kept the same as Sample 1. In Sample 4, the sodium hydroxide was increased to 61.9 g, while all the other conditions were kept the same as Sample 1.

TABLE 1

| Sample No. | ISOBAM ™ Type | Polymer Solid Content (%) | ISOBAM ™ Hydrolysis (%) | Viscosity (cps) |
|---|---|---|---|---|
| 1 | ISOBAM-18 ™ | 20 | 52.5 | 9500 |
| 2 | ISOBAM-18 ™ | 20 | 55.0 | |
| 3 | ISOBAM-18 ™ | 20 | 57.5 | 11600 |
| 4 | ISOBAM-18 ™ | 20 | 60.0 | 12400 |

Viscosity of the liquid superabsorbent precursor solutions was determined on a Rheometric Model DSR 200 stress rheometer using two 25 mm diameter, circular, parallel plates. The instrument was produced by Rheometric Scientific, Inc., Piscataway, N.J. The apparent viscosity of the superabsorbent precursor solution was measured during a stress sweep in a range of about 0.5 Pa to about 1000 Pa. Viscosity was also measured during a frequency sweep ranging from 0.1 to 100 rad/s, at a temperature of 22° C. The apparent viscosity at a shear rate of 0.1 l/s was reported.

The solution prepared in Sample 1 had a viscosity of 9500 centipoise (cps) at a shear rate of 0.1 l/s and a temperature of 22° C. The viscosity of the solution prepared in Sample 3 was 11,600 cps at a shear rate of 0.1 1/s and a temperature of 22° C. The solution made in Sample 4 was 12,400 cps at a shear rate of 0.1 l/s and a temperature of 22° C. All four solutions can be used for printing onto the substrate.

The printing resolution of the superabsorbent solutions is related to the solution viscosity. Generally, when the viscosity of the superabsorbent solutions is about 3000 to 4000 cps and below, the resolution of the printed regions is less than desired.

Example 3

By replacing one of the high-loft bonded carded web layers on the elastomeric high-loft bonded carded web with, for example, a meltspun web, and placing the superabsorbent on just the non-meltspun side, structures like headbands or wristbands have been made by heat sealing material 36 together forming a tube with the superabsorbent side out. Then the tube was turned inside out leaving the meltspun web without superabsorbent on it on the outside. This tube was then heat sealed together at the ends forming the sweatband. Of course, other fastening means like hook and loop (VELCRO) could be used to make the article adjustable. Since the material is elastic, other fastening means are not necessary, but are optional. To further improve the intake and distribution properties small amounts of wood pulp fluff can also be placed inside the sweatband to increase capillarity and thus help draw the fluid to the superabsorbent which then locks up the fluid.

Stirbar Retention Test Method

This test is a measure of superabsorbent attachment to a web when the superabsorbent has been fully swollen. This test was designed to simulate the worst conditions that a superabsorbent nonwoven composite would encounter inside of a swim pant.

The procedure for carrying out the stirbar retention test is as follows:
1. From the material being tested, cut out a 3 centimeter (cm) by 3 cm sample of known or determined substrate basis weight or of known initial SAP concentration.
2. Place the sample in an oven at 105 degrees Celsius for one hour to obtain an initial dry weight.
3. Measure and record the sample initial weight.
4. Soak the sample in an excess of 0.9 weight percent saline for 30 minutes.
5. Place the sample in a 250 ml beaker filled with 200 ml of tap water.
6. Stir at 400 rpm using a 9 millimeter (mm) by 37 mm magnetic, TEFLON-coated stirbar for 5 minutes.
7. Place the sample in oven overnight (16 hours) at 80 degrees Celsius.
8. Measure and record the sample final dry weight.
9. Calculate the percent retention using the following expression:

$$\% \, SAP \text{ retained} = 100 \times \left(1 - \frac{\text{initial weight} - \text{final weight}}{\text{initial weight} \times \text{initial } SAP \text{ concentration}}\right)$$

where "initial SAP concentration," if known, must be corrected to be on a 1 hour, 105 degree Celsius dry basis, or if the substrate baseis weight is known or can be determined is equal to:

1−(substrate basis weight in gsm×0.0009/initial weight).

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent, elastomeric material comprising:
   an elastomeric substrate comprising at least one open web facing; and
   a superabsorbent polymer including particles that encase fibers of the at least one open web facing, wherein at least some of the non-adhesively attached superabsorbent polymer is spread through at least about 50% of a thickness of the at least one open web facing.

2. The absorbent, elastomeric material of claim 1, wherein the absorbent, elastomeric material has a centrifuge retention capacity of between about 4 grams per gram and about 30 grams per gram.

3. The absorbent, elastomeric material of claim 1, wherein the absorbent, elastomeric material has a centrifuge retention capacity of between about 5 grams per grain and about 25 grams per gram.

4. The absorbent, elastomeric material of claim 1, wherein the absorbent, elastomeric material has a centrifuge retention capacity of between about 6 grams per grain and about 20 grams per gram.

5. The absorbent, elastomeric material of claim 1, wherein the elastomeric substrate further comprises a plurality of elastic strands laminated to the at least one open web facing.

6. The absorbent, elastomeric material of claim 1, wherein the elastomeric substrate further comprises an elastic film laminated to the at least one open web facing.

7. The absorbent elastomeric material of claim 1, wherein the elastomeric substrate further comprises an elastic foam laminated to the at least one open web facing.

8. The absorbent, elastomeric material of claim 1, comprising an elastic foam that functions as both the elastomeric substrate and the at least one open web facing.

9. The absorbent, elastomeric material of claim 1, wherein the at least one open web facing comprises a nonwoven material.

10. The absorbent, elastomeric material of claim 9, wherein the nonwoven material is selected from a group consisting of meltspun, meltblown. bonded carded web, elastomeric high-loft bonded carded web, and combinations thereof.

11. The absorbent, elastomeric material of claim 1, wherein the at least one open web facing has a volume fraction of less than about 0.05.

12. The absorbent, elastomeric material of claim 1, wherein the at least one open web facing has a volume fraction of less than about 0.04.

13. The absorbent, elastomeric material of claim 1, wherein the at least one open web facing has a volume fraction of less than about 0.02.

14. The absorbent, elastomeric material of claim 1, wherein the at least one open web facing has a mean pore size greater than about 200 microns.

15. The absorbent, elastomeric material of claim 1, wherein the at least one open web facing has a mean pore size greater than about 400 microns.

16. The absorbent, elastomeric material of claim 1, wherein at least some of the non-adhesively attached superabsorbent polymer is spread through at least about 75% of a thickness of the at least one open web facing.

17. The absorbent, elastomeric material of claim 1, wherein the absorbent, elastomeric material is incorporated into a structure of the absorbent article.

* * * * *